United States Patent [19]

Browne

[11] Patent Number: 5,357,970
[45] Date of Patent: Oct. 25, 1994

[54] METHOD FOR DETERMINING DOMINANT HEART RATES

[75] Inventor: David W. Browne, Tampa, Fla.

[73] Assignee: Critikon, Inc., Tampa, Fla.

[21] Appl. No.: 44,969

[22] Filed: Apr. 8, 1993

[51] Int. Cl.⁵ .............................................. A61B 5/024
[52] U.S. Cl. ................................ 128/706; 364/413.03; 364/413.05
[58] Field of Search ................... 128/696, 706, 698; 364/413.06, 413.03, 413.05

[56] References Cited

U.S. PATENT DOCUMENTS

| | | | |
|---|---|---|---|
| 3,978,856 | 9/1976 | Michel | 128/2.06 A |
| 4,239,048 | 12/1980 | Steuer | 128/666 |
| 4,478,224 | 10/1984 | Bailey | 128/706 |
| 4,549,551 | 10/1985 | Dyck et al. | 128/689 |
| 4,573,479 | 3/1986 | Tuccillo | 128/698 |
| 4,616,659 | 10/1986 | Prezas et al. | 128/706 |
| 4,777,959 | 10/1988 | Wallach et al. | 128/677 |
| 4,890,624 | 1/1990 | Ganguly et al. | 128/661.07 |
| 4,896,677 | 1/1990 | Kaneko et al. | 128/696 |
| 4,938,228 | 7/1990 | Righter et al. | 128/690 |
| 4,958,641 | 9/1990 | Digby et al. | 128/702 |
| 4,960,126 | 10/1990 | Conlon et al. | 128/633 |
| 4,964,410 | 10/1990 | Leahey et al. | 128/696 |
| 4,974,598 | 12/1990 | John | 128/696 |
| 4,974,601 | 12/1990 | Tranjan et al. | 128/696 |
| 4,977,899 | 12/1990 | Digby et al. | 128/702 |
| 4,979,110 | 12/1990 | Albrecht et al. | 364/413.03 |
| 5,002,052 | 3/1991 | Haluska | 128/419 |
| 5,042,499 | 8/1991 | Frank et al. | 128/698 |
| 5,090,418 | 2/1992 | Squires et al. | 128/702 |
| 5,139,027 | 8/1992 | Lindecrantz | 128/696 |
| 5,190,047 | 3/1993 | Odagiri et al. | 128/687 |

Primary Examiner—Kyle L. Howell
Assistant Examiner—Kennedy J. Schaetzle
Attorney, Agent, or Firm—Dominik, Stein, Saccocio, Reese, Colitz & Van Der Wall

[57] ABSTRACT

A method for determining a dominant heart rate from a series of beat triggers representative of a mixed series of normal heart beats and non-arrhythmic activities, with the beat triggers being determined at a specific sampling rate defining sample intervals, comprising the steps of: framing a window to include a portion of the series of beat triggers and to be beat-aligned with a first beat trigger and a last beat trigger, the window thereby defining a plurality of trigger intervals for respective adjacent beat triggers, with each trigger interval containing a plurality of the sample intervals existing between the respective adjacent beat triggers; summing the windowed sample intervals; for each of the trigger intervals, computing a weight factor based upon the ratio of the summed windowed sample intervals to the number of sample intervals within that trigger interval; grouping the trigger intervals according to the weight factors; computing the percentage of the window that each group of weight factors constitutes to determine the dominant group containing the dominant beat triggers; and analyzing the dominant beat triggers within the dominant group to determine the dominant heart rate.

12 Claims, 4 Drawing Sheets

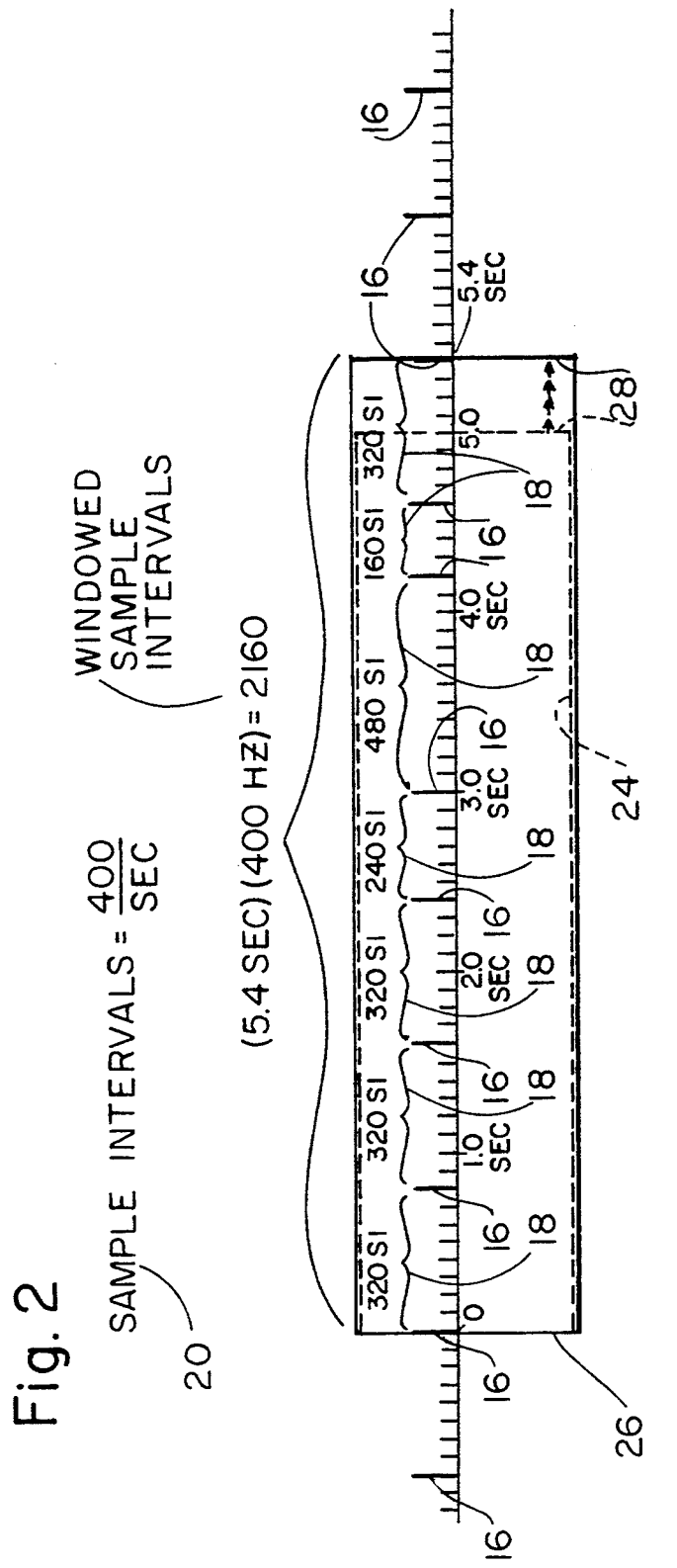

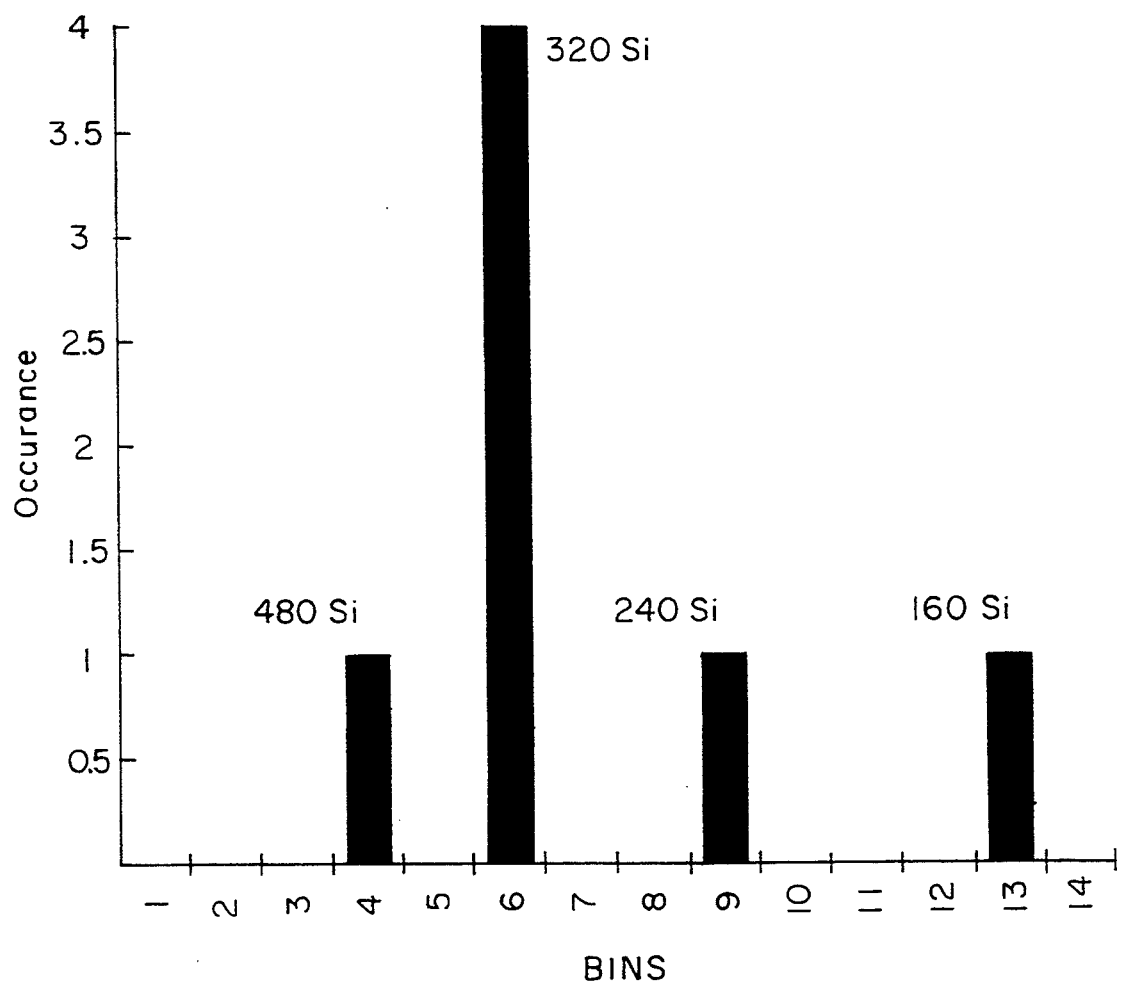

METHOD FOR DETERMINING DOMINANT HEART RATES

BACKGROUND OF THE INVENTION

1. Field of the Invention

This invention relates to methods for determining the heart rate of a patient. More particularly, this invention relates to methods for rapidly determining the heart rate of a patient over a short period or window of time for immediate display to the attending physician or nurse.

2. Description of the Background Art

Presently there exist many methods or techniques for determining the heart rate of a patient. The simplest method comprises the manual averaging of heart beats over a period or "window" of time by multiplying by the number of beats by a multiplier to determine an average heart beat interval that is then used to compute the number of heart beats per minute. Longer periods or windows may be employed for more accurate heart rate determination. The longer periods necessarily result in increased response times for reporting and acting upon changing rates.

For the past decades, electronic or computerized heart rate monitors have been developed for automatically determining the average heart rate of the patient and for displaying the heart rate to the attending physician or nurse. Most of these monitors employ techniques for identifying or characterizing non-arrhythmic artifacts and activities that would otherwise skew the averaging of the heart rate. Common non-arrhythmic activities include PVCs, non-blanked pacer spikes, fast flushes, and short noisy or unstable regions.

By way of example, as shown in U.S. Pat. 4,478,224, improved heart rate determinations may be obtained by monitoring the patient's EKG signal to detect heartbeat artifacts and for producing a corresponding inhibit signal. The inhibit signal is supplied to the heart rate monitor to inhibit the heart rate determinations whenever the artifacts are detected. During operation, the heart rate monitor measures the time intervals between successive heartbeats and estimates heartbeat rate based on a plurality of such time interval measurements. If the inhibit signal ever occurs, indicating the occurrence of a heartbeat artifact, the inhibit signal inhibits the monitor from continuing to measure the current heartbeat interval.

Thereafter, when the inhibit signal terminates, indicating that the artifact is no longer present, the monitor resumes measuring time intervals after the occurrence of the next heartbeat.

As noted above, a large window results in a more accurate heart rate calculation since the number of heart beats occurring within the window is higher and the calculation is less suspectable to skewing by non-arrhythmic activities. However, the larger the window is in time, the longer the rate calculation delay. Hence, the size of the window is often critical to the time delay between rate calculations and display updates.

On the one hand, design goals often seek to minimize the window so that the heart rate may be updated and displayed in what appears as real time. On the other hand, the longer the window, the more accurate the determination of the heart rate can be, especially if the heart beats are averaged over the window.

Therefore, it is an object of this invention to provide an improvement which overcomes the aforementioned inadequacies of the prior art methods and provides an improvement which is a significant contribution to the advancement of the methods for determining heart rates.

Another object of this invention is to more accurately determine the running rate of a heart over a short period or window of time in the presence of non-arrhythmic activities such as PVCs, non-blanked pacer spikes, fast flushes, and short noisy or unstable regions.

Another object of this invention is to minimize or eliminate the non-arrhythmic activities from the calculation of the dominant heart rate during the window of time, so that the dominant heart rate calculation is not excessively skewed by the non-arrhythmic activities.

Another object of this invention is to provide a method for determining a dominant heart rate from a series of beat triggers representative of a mixed series of normal heart beats and non-arrhythmic activities.

Another object of this invention is to provide a method for determining a dominant heart rate from a series of beat triggers representative of a mixed series of normal heart beats and non-arrhythmic activities, with the beat triggers being determined at a specific sampling rate defining sample intervals, comprising the steps of framing a window to include a portion of the series of beat triggers and to be beat-aligned with a first beat trigger and a last beat trigger, the window thereby defining a plurality of trigger intervals for respective adjacent beat triggers, with each trigger interval containing a plurality of the sample intervals existing between the respective adjacent beat triggers; summing the windowed sample intervals; for each of the trigger intervals, computing a weight factor based upon the ratio of the summed windowed sample intervals to the number of sample intervals within that trigger interval; grouping the weight factors; computing the percentage of the window that each group of weight factors constitutes to determine the dominant group containing the dominant beat triggers; and analyzing the dominant beat triggers within the dominant group to determine the dominant heart rate.

The foregoing has outlined some of the pertinent objects of the invention. These objects should be construed to merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention and the detailed description of the preferred embodiment in addition to the scope of the invention defined by the claims taken in conjunction with the accompanying drawings.

SUMMARY OF THE INVENTION

For the purpose of summarizing the invention, the invention comprises a method for determining the dominant heart rate of a patient over a short window of time for display to the attending physician or nurse. More particularly, the method of the invention determines the dominant heart rate from a series of beat triggers. The beat triggers may be generated by prior art heart rate monitors and are representative of a mixed series of normal heart beats and non-arrhythmic activities such as PVCs, non-blanked pacer spikes, fast flushes, and short noisy or unstable regions.

The method of the invention is founded upon the concept that an interval of time between adjacent beat triggers represents only a percentage of a given window of time, assuming that the window is large enough to incorporate a representative sampling of such trigger intervals. A weight factor may be derived for each trigger interval because each trigger interval may be viewed as a percentage of the window itself. By computing the weight factor for each of the trigger intervals that occurred within the window of time based upon the sum of the trigger intervals that came within the window, the trigger intervals may be grouped or "binned" together according to their respective weight factors.

Analyzing the ratio in which these weight factors occurred over their represented weight, results in a way to quantify the most prevalent trigger intervals. Specifically, the largest ratio represents the dominant trigger intervals within the window of time. The dominant trigger intervals may then be averaged to obtain a most dominant trigger interval. This most dominant trigger interval may then be used to calculate the dominant heart rate for the window period of time for immediate display to the attending physician or nurse.

Importantly, the method of the invention quantifies the most dominant trigger intervals, thereby inherently rejecting non-arrhythmic activities without characterizing each. The inherent rejecting of non-arrhythmic activities therefore minimizes or eliminates the skewing of the computation of the dominant heart rate that would otherwise result. Importantly, there is no requirement to even attempt to characterize the non-arrhythmic activity in order to reject them. More consistent heart rate monitoring is therefore obtained by employing the method of the invention into a heart rate monitor.

Finally, while not necessary for heart rate calculation, it is noted that the binning of the trigger intervals according to their respective weight factors also tends to bin similar non-arrhythmic activities together. The trigger intervals within the respective bins may then be analyzed to attempt to characterize the specific nature of the non-arrhythmic activity.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other methods for carrying out the same purposes of the present invention. It should also be realized by those skilled in the art that such equivalent methods do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which:

FIG. 2 is a timing diagram of a series of beat triggers produced by the heart rate monitor that is representative of a mixed series of normal heart beats and non-arrhythmic activities overlaid onto the sample intervals defined by the monitor's sampling rate, with a window framed thereto according to the method of the present invention by beat-aligning the leftmost frame of a minimum-sized window with a first beat trigger and then increasing the rightmost frame of the minimum-sized window such that the rightmost frame of the window is beat-aligned with the next beat trigger after the minimum-sized window, the window thereby encompassing a plurality of trigger intervals for respective adjacent beat triggers, with each trigger interval containing a plurality of the sample intervals that exist between the respective adjacent beat triggers;

FIG. 3 graphically illustrates the weighting and grouping (binning) of the trigger intervals based upon the ratio of the summed windowed sample intervals to the number of sample intervals within the trigger interval.

Similar reference characters refer to similar parts throughout the several views of the drawings.

DETAILED DESCRIPTION OF THE PREFERRED METHOD OF THE INVENTION

Figure 1B:
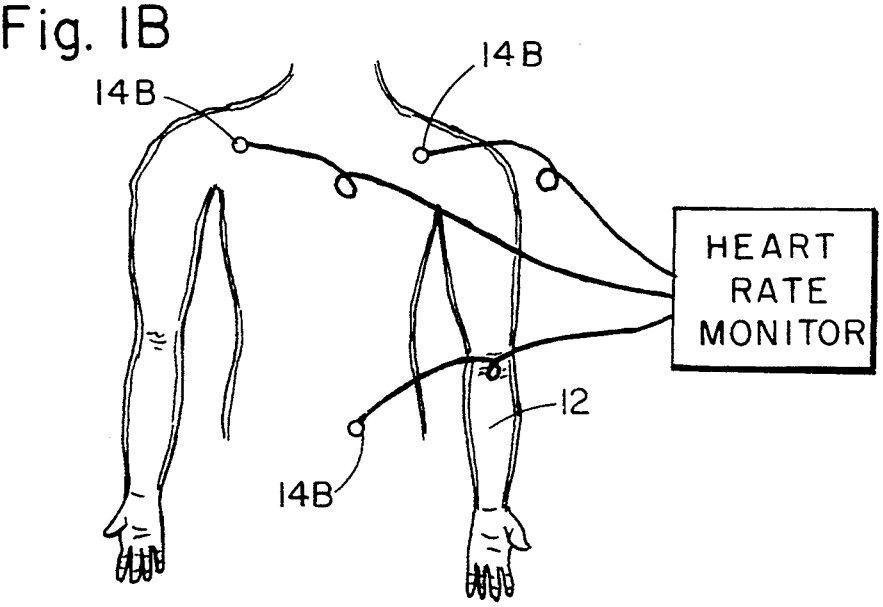
FIGS. 1A, 1B and 1C are diagrammatic views of several types of heart rate monitors connected to a patient.
Figure 1A:
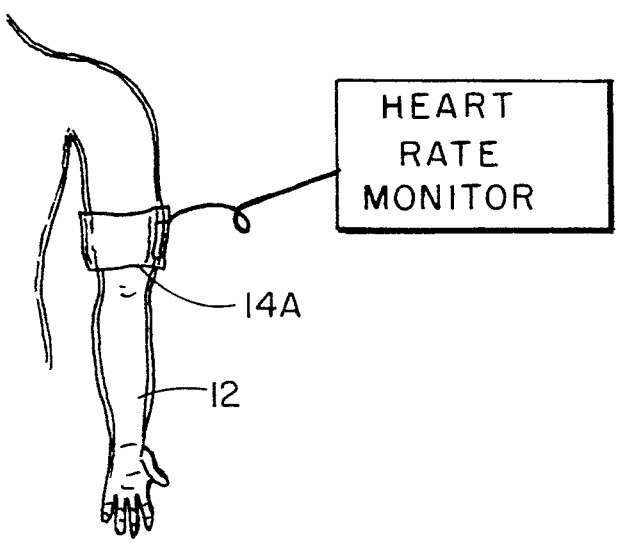
Figure 1C:
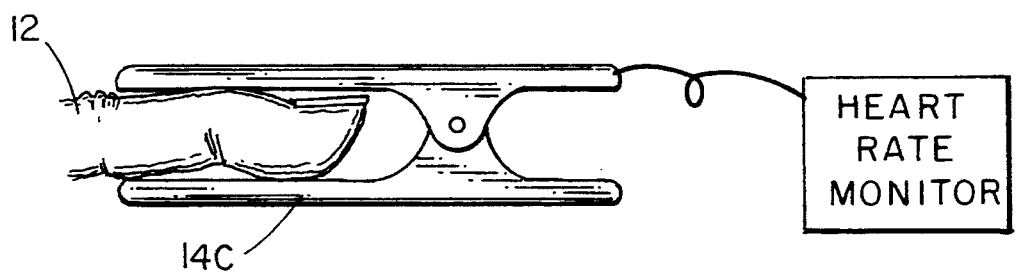

As shown in FIGS. 1A, 1B and 1C, a conventional heart rate monitor 10 is operatively connected to the patient 12 whose heart rate is to be monitored. Without departing the spirit and scope of this invention, any suitable monitor 10 may be employed to detect the beats of patient's 12 heart by means of any suitable transducer 14 positioned intravenously, subcutaneously or exteriorly to the patient 12. For example, the transducer 14 may comprise a blood-pressue cuff 14A, ECG electrodes 14B or finger pulse oximeter 14C. The transducer 14 is sampled according to a predefined sampling rate of the monitor 10.

As shown in FIG. 2, in practice, the sampling of the patient's 12 heart rate produces a series of beat triggers 16 comprising a mixture of normal heart beats and undesired non-arrhythmic activities caused by PVCs, non-blanked pacer spikes, fast flushes, and short noisy or unstable heart beats. A trigger interval 18 is defined as the time between the adjacent beat triggers 16. Dependent upon the sampling rate of the monitor 10, each trigger interval 18 encompasses a plurality of sample intervals 20 defined as the constant time between sampling of the transducer 14.

The method of the invention may be employed within the monitor 10 by a suitable microcomputer, array processor or discrete electrical components (not shown). The method comprises the step of first framing a window 22 to the series of the beat triggers 16. This beat-aligning of the window is accomplished by predefining a minimum-sized window 24, such as one five seconds in length. The leftmost frame 26 of the minimum-sized window 24 is beat-aligned with one of the first beat triggers 16. With this left alignment, it is noted that the rightmost frame 28 of the minimum-sized window 24 would not likely be aligned with a beat trigger 16. Hence, the rightmost frame 28 of the minimum-sized window 24 is increased in size until it is beat-aligned with the next beat trigger 16 after the minimum-sized window 24. The window 22 under examination therefore comprises the length of this increased minimum-sized window 24.

It is also noted that the precise size or length of the window 22 may be determined by summing the sample intervals 20 windowed therein since the sample intervals 20 are of a constant length as determined by the sampling rate. Likewise, it is noted that the precise lengths of the trigger intervals 18 may determined by summing the sample intervals 20 encompassed by each, and then the length of the window 22 may be determined by summing the trigger intervals 18.

For each of the trigger intervals 18, a weight factor is computed. Each of the weight factors is equal to the ratio of the length of the window 22 (i.e. the sum of the windowed sample intervals) to the number of sample intervals 20 encompassed within that trigger interval 18 itself.

The trigger intervals 18 are then grouped or "binned" according to their respective weight factors. In a preferred embodiment, the bins are then numbered by first determining the maximum number of sample intervals 20 that would occur for a maximum-anticipated heart rate (e.g. 350 beats per minute) at the specific sample rate of the monitor 10. The ratio of the number of the windowed sample intervals 20 to such maximum number of sample intervals 20 is then computed. The maximum numbered bin is then numbered to a whole number that is closest to this ratio. The remaining bins are then numbered so that the ranges of weight factors are evenly distributed from bin numbered one to the maximum numbered bin.

By way of example, this binning of weight factors according to the method of the invention may proceed as follows:

For a 400 hertz sampling rate and a maximum-anticipated heart rate of 350 BPM, the number of sample intervals 20 is computed as:

$$\frac{400 \text{ Hz} * 60 \text{ sec}}{350 \text{ BPM}} = 68.57 \text{ Sample Intervals}$$

Then, by taking a five second minimum-sized window 24 and dividing it by this number of sample intervals, the maximum number of sample intervals 20 that can occur within the trigger intervals 18 at the maximum-anticipated heart rate is computed as:

$$\frac{400 \text{ Hz} * 5 \text{ sec}}{69 \text{ Sample Intervals}} = 28.98 \text{ Occurrences}$$

Rounding to the closest whole number, this results in a weight factor of 29 assigned to trigger intervals 18 containing 69 sample intervals. The bins are therefore numbered from 1 to 29. All of the weight factors are grouped into ranges and the ranges are then evenly distributed throughout the numbered bins as set forth the following Table 1:

| NUMBERED BIN | SAMPLE INTERVALS WITHIN TRIGGER INTERVAL | BEAT TRIGGERS |
|---|---|---|
| 1 | 4000–1412 | 6–17 |
| 2 | 1333–828 | 18–29 |
| 3 | 800–585 | 30–41 |
| 4 | 571–453 | 42–53 |
| 5 | 444–369 | 54–65 |
| 6 | 364–312 | 66–77 |
| 7 | 308–270 | 78–89 |
| 8 | 267–238 | 90–101 |
| 9 | 235–212 | 102–113 |
| 10 | 211–190 | 114–125 |
| 11 | 190–174 | 126–137 |
| 12 | 174–161 | 138–149 |
| 13 | 160–149 | 150–161 |
| 14 | 148–139 | 162–173 |
| 15 | 138–130 | 174–185 |
| 16 | 129–122 | 186–197 |
| 17 | 121–115 | 198–209 |
| 18 | 114–109 | 210–221 |
| 19 | 108–103 | 222–233 |
| 20 | 103–98 | 234–245 |
| 21 | 98–93 | 246–257 |
| 22 | 93–89 | 258–269 |
| 23 | 89–85 | 270–281 |
| 24 | 85–82 | 282–293 |
| 25 | 82–79 | 294–305 |
| 26 | 78–76 | 306–317 |
| 27 | 75–73 | 318–329 |
| 28 | 73–70 | 330–341 |
| 29 | 70–68 | 342–351 |

After the binning of the weight factors is complete, the method of the invention proceeds to compute the percentage of the window 22 that each numbered bin represents to determine which of the numbered bins contains the dominant trigger intervals 18. This step of the method is first repeated for each numbered bin by counting the number of trigger intervals 18 contained within that numbered bin and then dividing that number of trigger intervals 18 by that numbered bin's bin number to compute a percentage of the window 22 that that numbered bin represents.

The numbered bin or bins constituting the highest percentage or percentages of the window are then selected as the dominant numbered bin or bins containing the dominant trigger intervals 18. Preferably, this selection may be based upon the numbered bin that constitutes the highest percentage, thereby identifying the most dominant numbered bin. However, if none of the numbered bins constitutes a highest percentage, then the adjacent numbered bin constituting the highest percentages may be selected as the dominant numbered bins.

All of the dominant trigger intervals 18 within the most dominant numbered bin, or in the dominant numbered bins, may then be averaged together to obtain an averaged dominant trigger interval 18. It is this averaged dominant trigger interval 18 that is then used to compute the patient's heart rate, By way of example in relation to FIGS. 2 and 3 and Table 1, it is seen that there are four trigger intervals 18 containing 320 sample intervals 20 that are binned into bin number 6, one trigger interval 18 containing 240 sample intervals 20 that is binned into bin number 8, one trigger interval 18 containing 480 sample intervals 20 that is binned into bin number 4, and one trigger interval 20 containing 160 sample intervals 20 that is binned into bin number 13. The computation of the percentage of the window 22 that each numbered bin represents to determine which of the numbered bins contains the dominant trigger intervals 18 can be tabulated in Table 2 as follows:

| BIN NUMBER | NUMBER OF OCCURRENCES OF TRIGGER INTERVALS | PERCENTAGE OF THE WINDOW THAT NUMBERED BIN REPRESENTS |
| --- | --- | --- |
| 6 | 4 | 4/6 = 66% |
| 9 | 1 | 1/9 = 11% |
| 4 | 1 | 1/4 = 25% |
| 13 | 1 | 1/13 = 8% |

Figure 4:
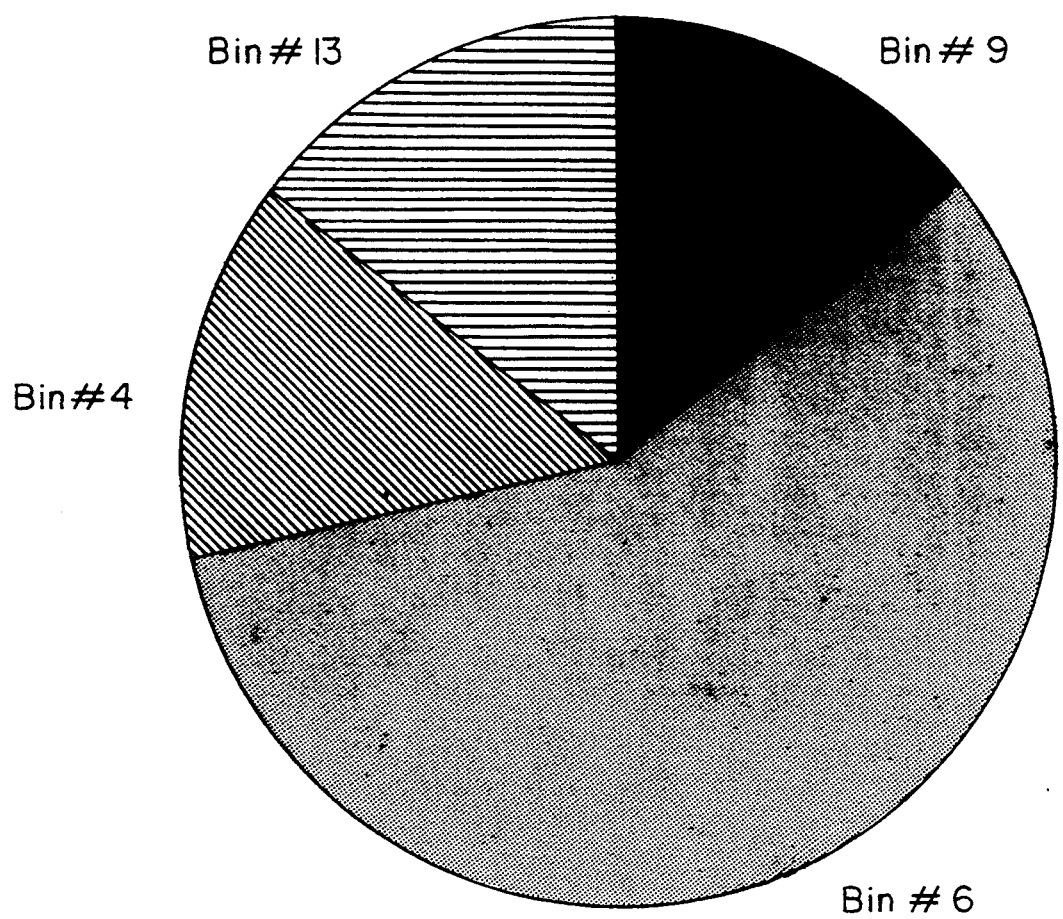
FIG. 4 is a chart showing the percentage of the window that each group of trigger intervals constitutes thereby illustrating which group contains the dominant beat triggers.

Thus, as shown in the pie-chart of FIG. 4, it is seen that bin numbered 6 constitutes the highest percentage of the window 22 is therefore selected as the dominant numbered bin containing the dominant trigger intervals 18. If the dominant trigger intervals 18 within bin numbered 6 were not all equal to 320 sample intervals 20 as illustrated, but varied somewhat (e.g. 340 or 360 sample intervals), they may then be averaged together to obtain an averaged dominant trigger interval. This averaged dominant trigger interval would then used to compute the heart rate of the patient.

It should be appreciated that the above-described method of the invention substantially eliminates the skewing of the heart rate calculations attributable to non-arrhythmic activities because the non-arrhythmic activities do not, as a norm, generate a dominant rate themselves and even if they did, it would be a small representation of the total window 22. Specifically, the dominant trigger intervals representative of normal heart beats would have more intervals that fall into its grouping and therefore consume more of the window 22. The undesired trigger intervals 18 may even be across a whole window 22 but they would be included into several of the weight factors thereby dispersing the weight of the window 22 over many bins and not all into the otherwise dominant bin. This feature of the method of the invention may be utilized to reject undesired trigger intervals representative of noisy or abnormal intervals and to flag such noisy regions and tag abnormal events.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of the method and the combination and arrangement of steps may be resorted to without departing from the spirit and scope of the invention.

Now that the invention has been described,
What is claimed is:

1. A method for determining a dominant heart rate from a series of beat triggers representative of a mixed series of normal heart beats and non-arrhythmic activities, with the beat triggers being determined at a specific sampling rate defining sample intervals, comprising the steps of:

framing a window to include a portion of the series of beat triggers and to be beat-aligned with a first beat trigger and a last beat trigger, the window thereby defining a plurality of trigger intervals for respective adjacent beat triggers, with each trigger interval containing a plurality of the sample intervals existing between the respective adjacent beat triggers;

summing the windowed sample intervals;

for each of the trigger intervals, computing a weight factor based upon the ratio of the summed windowed sample intervals to the number of sample intervals within that trigger interval;

grouping the trigger intervals according to the weight factors;

computing the percentage of the window that each group of weight factors constitutes to determine the dominant group containing the dominant beat triggers; and analyzing the dominant beat triggers within the dominant group to determine the dominant heart rate.

2. The method as set forth in claim 1, wherein the step of framing a window to include a portion of the series of beat triggers and to be beat-aligned with a first beat trigger and a last beat trigger, comprises the step of sizing the window including the steps of aligning a leftmost frame of the window with the first beat trigger and aligning a rightmost frame of the window with the last beat trigger.

3. The method as set forth in claim 2, wherein the step of sizing the window comprises the step of predetermining a minimum-sized window, aligning the leftmost frame of the minimum-sized window with the first beat trigger and then increasing the rightmost frame of the minimum-sized window such that the rightmost frame of the window is aligned with the next beat trigger after the minimum-sized window.

4. The method as set forth in claim 1, wherein the steps of grouping the weight factors and computing the percentage of the window that each group of weight factors constitutes to determine the dominant group, comprise the step of:

numbering bins to correspond to the weight factors; and computing the percentage of the window that each numbered bin represents to determine the dominant numbered bin containing the dominant beat triggers.

5. The method as set forth in claim 4, wherein the step of numbering bins to correspond to the weight factors, comprises the steps of determining the maximum number of sample intervals that occur for a maximum-anticipated heart rate at the specific sampling rate, computing the ratio of the number of windowed sample intervals to such maximum number of sample intervals, numbering the maximum numbered bin to the closest whole number to the ratio, and then evenly distributing the groups of weight factors in increasing order from numbered bin one to the maximum numbered bin.

6. The method as set forth in claim 5, wherein the sampling rate is approximately 400 hertz and wherein the minimum-sized window comprises approximately five seconds.

7. The method as set forth in claim 6, wherein the step of numbering bins to respective increasing bin numbers, comprises the step of numbering bins to substantially a range of 1-29.

8. The method as set forth in claim 4, wherein the step of computing the percentage of the window that each numbered bin represents to determine the dominant numbered bin containing the dominant beat triggers, comprises, for each numbered bin, the step of determining the number of trigger intervals contained within that numbered bin and then dividing that number of trigger intervals by that numbered bin's bin number to compute the percentage of the window that that numbered bin represents.

9. The method as set forth in claim 8, wherein the step of computing the percentage of the window that each numbered bin represents to determine which numbered bin contains the dominant beat triggers, further comprises the step of selecting the numbered bins constituting the highest percentages of the window as the dominant numbered bins containing the dominant beat triggers.

10. The method as set forth in claim 9, wherein the step of analyzing the beat triggers within the dominant numbered bins to determine the dominant heart rate comprises the step of averaging the dominant beat triggers within the dominant numbered bins to compute the dominant heart rate.

11. The method as set forth in claim 8, wherein the step of analyzing the beat triggers within the dominant numbered bins to determine the dominant heart rate comprises the step of selecting the most dominant bin constituting the highest percentage.

12. The method as set forth in claim 1, wherein the step of analyzing the beat triggers within the dominant group to determine the dominant heart rate comprises the step of averaging the dominant beat triggers within the most dominant group to compute the most dominant heart rate.

* * * * *